United States Patent [19]
Glowinski et al.

[11] Patent Number: 5,868,674
[45] Date of Patent: Feb. 9, 1999

[54] MRI-SYSTEM AND CATHETER FOR INTERVENTIONAL PROCEDURES

[75] Inventors: Arndt Glowinski, Aachen, Germany; Johannes J. Van Vaals, Eindhoven, Netherlands

[73] Assignee: U.S. Philips Corporation, New York, N.Y.

[21] Appl. No.: 754,358

[22] Filed: Nov. 22, 1996

[30] Foreign Application Priority Data

Nov. 24, 1995 [EP] European Pat. Off. .............. 95203229

[51] Int. Cl.⁶ ..................................................... A61B 5/05
[52] U.S. Cl. ......................... 600/410; 600/421; 600/424; 324/318; 324/322
[58] Field of Search ............................. 128/653.2, 653.5, 128/899, 653.1; 324/318, 322; 600/407, 410, 424, 409, 421

[56] References Cited

U.S. PATENT DOCUMENTS

| | | | |
|---|---|---|---|
| 5,271,400 | 12/1993 | Dumoulin et al. ................... | 128/653.2 |
| 5,429,132 | 7/1995 | Guy et al. ............................ | 128/653.1 |
| 5,437,277 | 8/1995 | Dumoulin et al. ................... | 128/653.1 |
| 5,443,066 | 8/1995 | Dumoulin et al. ................... | 128/653.1 |
| 5,447,156 | 9/1995 | Dumoulin et al. ................... | 128/653.2 |
| 5,562,698 | 10/1996 | Parker ................................. | 606/120 |
| 5,644,234 | 7/1997 | Rasche et al. ...................... | 324/318 |
| 5,647,361 | 7/1997 | Damadian ........................... | 128/653.2 |

*Primary Examiner*—Marvin M. Lateef
*Assistant Examiner*—Eleni Maria Mantis Mercader
*Attorney, Agent, or Firm*—Dwight H. Renfrew, Jr.

[57] ABSTRACT

An MR system for interventional procedures, includes an MR imaging device and an interventional instrument, for example a catheter. The MR device is arranged to acquire images of a part of an object. The entire catheter can be imaged in an MR image by providing a conductor loop which comprises two non-magnetic conductors which are situated at some distance from one another underneath the surface of the catheter, and extend along substantially the entire length of the catheter. Furthermore, the catheter may be provided with a conductor loop and a coil in a location on the catheter. By separate adjustment of the current flowing through the conductor loop and the coil, it is possible to image the location on the catheter with a contrast which deviates from that of the remainder of the catheter.

21 Claims, 4 Drawing Sheets

2

MRI-SYSTEM AND CATHETER FOR INTERVENTIONAL PROCEDURES

BACKGROUND OF THE INVENTION

1. Field of the Invention

The invention relates to an MR system for interventional procedures, including an MR imaging device which is arranged to acquire images of a part of an object and includes a magnet for generating a steady magnetic field, a gradient system for generating temporary magnetic gradient fields, and an interventional instrument or device, for example, a catheter, which includes means for generating an additional magnetic field. This invention also relates to an interventional instrument for cooperation with MR imaging device.

2. Description of the Related Art

An MR system of this kind is known from U.S. Pat. No. 4,572,198. In the known MR system the catheter is positioned, in cooperation with the MR device, so as to subject the object to an interventional procedure for which the catheter has been designed. This is, for example balloon angioplasty of a patient. Furthermore, in the known MR system the image processing unit determines the position of the catheter tip in the object on the basis of two successive MR images of the patient. The additional magnetic field is then switched off during the generating of the MR signals for the reconstruction of a first image, whereas it is switched on during the generating of the MR signals for the reconstruction of a next MR image. The additional magnetic field generated by a coil provided in the catheter tip disturbs the magnetic fields generated by the MR device, so that a difference arises between the two MR images. The processing unit determines the position of the catheter tip on the basis of the difference between the two MR images. Subsequently, via a cursor the position of the catheter tip is superposed on the MR image of the body so as to be displayed on a monitor.

It is a drawback of the known system that only the catheter tip is imaged in an MR image.

SUMMARY OF THE INVENTION

It is inter alia an object of the invention to image the entire catheter in as far as it is present within the object.

To this end, an MR system in accordance with the invention is characterized in that the means for generating the additional magnetic field comprise a conductor loop with two non-magnetic, spaced apart, conductors extending along substantially the length of the catheter.

As a result of the formation of a conductor loop for generating the additional magnetic field, the magnetic fields generated by the MR device are disturbed in a small region extending along the catheter. The entire catheter can be imaged in an MR image due to the application of the additional magnetic field by the conductor loop in the catheter. It is also to be noted that in the context of the present patent application a catheter is to be understood to mean also other interventional instruments whose positioning is of importance, for example instruments such as a guide wire and biopsy needles. The strength of the additional magnetic field can be adjusted by adjustment of a current through the conductor loop. A desired contrast can thus be adjusted or the contrast can be modulated. The advantage thereof consists in that the same contrast of the catheter can be adjusted for different imaging techniques with different sensitivities to disturbances caused by the additional magnetic field or by different positions of the catheter relative to the static magnetic field. The strength of the additional magnetic field is also determined by the distance between the two conductors of the conductor loop.

A difference with respect to the catheter known from the cited U.S. Pat. No. 4,572,198 consists in that in the known catheter disturbing effects on the magnetic field of the MR device are counteracted by using paired conductors extending along the catheter to the coil in the catheter tip, so that only a disturbance of the magnetic field in the vicinity of the catheter tip is imaged in the MR image.

A catheter which can also be imaged in its entirety in an MR image is known from U.S. Pat. No. 4,989,608. However, in this known catheter a permanent magnetic field is generated by ferromagnetic particles distributed over the length of the catheter. It is a drawback of this known catheter that the strength of the disturbing magnetic field cannot be adjusted so that the contrast with which the catheter is imaged in an MR image is dependent only on the properties of the tissue in the vicinity of the catheter, on the position of the catheter relative to the steady magnetic field, and on the imaging pulse sequences used. It is a further drawback that the sensitivity is too high for some imaging pulse sequences whereas for other imaging sequences it is too low for visualization of the catheter in an MR image.

A special embodiment of an MR system in accordance with the invention is characterized in that the conductor loop is connected to a variable voltage power supply.

As a result of the use of a variable-voltage power supply, the current in the conductor loop can be simply adjusted, thus enabling adjustment of the contrast of the catheter in an image.

Another embodiment of an MR system in accordance with the invention is characterized in that the catheter is provided with a coil for generating a second additional magnetic field which deviates from the first additional magnetic field. As a result of the presence of a coil in a location in the catheter, the second additional magnetic field can generate a second disturbance in the magnetic field in the vicinity of the location of the coil, so that in an MR image this location can be imaged with a contrast which deviates from that of the remainder of the catheter.

Another embodiment of an MR-system according to the invention is characterized in that the distance between the conductors along the catheter is different for some parts of the catheter. By varying the distance and thereby the strength of the disturbance along the catheter a kind of pattern, can be visualized in an MR-image, so that the catheter is better recognizable.

Another embodiment according to the invention is characterized in that the conductors of the conductor loop being curled in a helix configuration. As a result the induced RF currents in the conductor loop are reduced, which RF currents are induced during generation of RF signals in the MR system.

Another embodiment according to the invention is characterized in that the conductors of the conductor loop being curled in an anti-parallel helix configuration. As a result, a torsion on the catheter is reduced when an electromagnetic force on the conductors is present due to a direct current in a steady magnetic field.

A further embodiment of an MR system in accordance with the invention is characterized in that the MR device is arranged to execute the following steps:

a) generating MR signals in order to determine temporally successive first and second MR images, b) generating the first and/or the second additional magnetic field during the generating of MR signals for determining the second MR image, c) receiving the MR signals generated, d) processing the MR signals received so as to form the first and the second MR image, e) determining a position of the catheter within the object on the basis of the first and the second MR image.

This step enables accurate determination of the position of the catheter from the difference between two MR images. The difference between the MR images is caused by the fact that the additional magnetic field is switched off during the generating of the MR signals for a first image whereas it is switched on during the generating of the MR signals for a second image.

A further embodiment of an MR system in accordance with the invention is characterized in that it is also arranged to derive images from MR signals by means of a so-called keyhole technique. This step offers a reduction of the exposure time of two temporally successive images. This technique is known inter alia from EP-A 543468. The keyhole technique according to the cited patent application utilizes the MR signal set associated with the complete k-space so as to acquire a first image. Subsequently, only a part of the k-space is used to generate new MR signals which are subsequently substituted in the positions of the MR signals of the previously obtained MR signal set which are associated with the relevant part of the k-space. From this updated MR signal set a temporally subsequent image is determined. This method is capable of forming quasi real time images in the described manner, so that the catheter can be tracked during displacement within the object.

A further embodiment of an MR system in accordance with the invention is characterized in that the control unit is arranged to adapt a position of a region to be imaged, in which the catheter is present, to the catheter position determined. As a result of this step, the region to be imaged follows the catheter in the object. When the position is quickly determined and the position of the region to be imaged is adjusted, moreover, the catheter can be continuously tracked so that it is continuously imaged in an MR image during displacement.

The invention also relates to a catheter which is characterized in that in order to generate an additional magnetic field the catheter is provided with conductors of a non-magnetic material which extend along substantially its entire length, are situated at a given distance from one another, are interconnected at the end of the catheter and hence form a conductor loop.

A further embodiment of the catheter in accordance with the invention is characterized in that the conductors of the conductor loop being curled in a helix configuration.

A further embodiment of the catheter in accordance with the invention is characterized in that the conductors of the conductor loop being curled in an anti-parallel helix configuration.

A further embodiment of the catheter in accordance with the invention is characterized in that the conductor loop is connected to a variable-voltage power supply. A further embodiment of the catheter in accordance with the invention is characterized in that the catheter comprises a coil for generating a second additional magnetic field which deviates from the first additional magnetic field.

These and other aspects of the invention will be apparent from and elucidated with reference to the embodiments described hereinafter.

DESCRIPTION OF THE PREFERRED EMBODIMENTS

Figure 1:
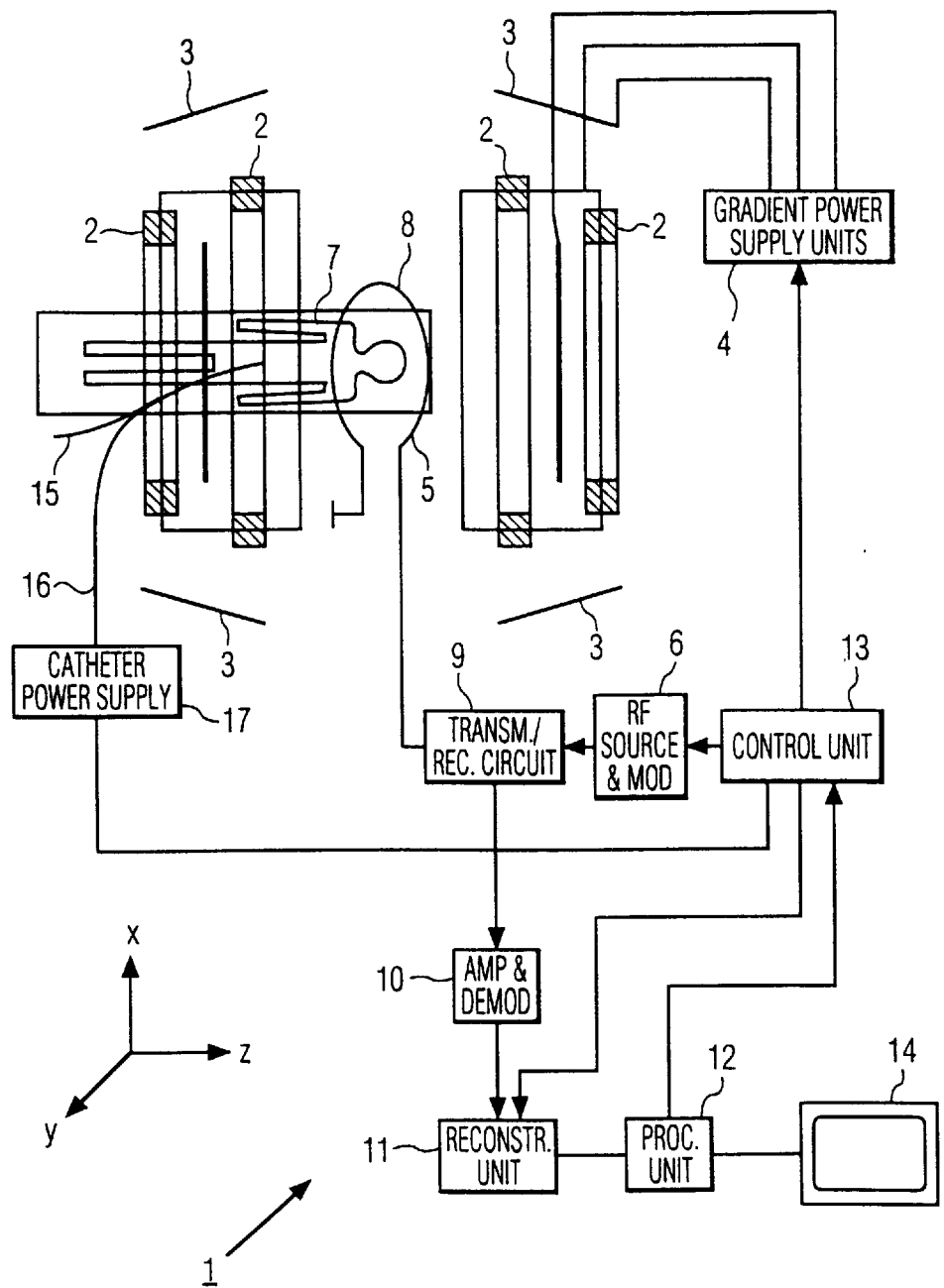
FIG. 1 shows an MR system.

FIG. 1 shows a magnetic resonance system 1 comprising an MR device 1 and a catheter 15. The MR device 1 comprises a first magnet system 2 for generating a static magnetic field, a second magnet system 3 for generating gradient fields, and power supply units 4 for the first magnet system 2 and the second magnet system 3. The z-direction of the coordinate system shown corresponds to the direction of the steady magnetic field in the magnet system 2. An RF transmitter coil 5 serves to generate RF magnetic fields and is connected to an RF source and modulator 6. A receiver coil 8 serves to receive the MR signal generated by the RF field in the object 7 to be examined, for example a patient. The receiver coil 8 and RF transmitter coil 5 may be one and the same coil. The magnet system 2 encloses an examination space which is large enough to accommodate the patient to be examined. The RF transmitter coil 5 is arranged around a part of the patient within the examination space. The RF transmitter coil 5 is connected to a signal amplification and demodulation unit 10 via a transmitter/receiver circuit 9. The phase and amplitude derived therefrom are further processed. The image reconstruction unit 11 processes the signals presented so as to form an image. This image is displayed, via an image processing unit 12, for example on a monitor 14. The control unit 13 controls a modulator 6 for the RF transmitter, the power supply units 4 for the magnetic gradient fields, and the image reconstruction unit 11. Images processing unit 12 determines the position of a catheter 15 inserted into the body and supplies position information to control unit 13. In accordance with the invention catheter 15 comprises a conductor loop 16 connected to a catheter power supply unit 17.

Figure 2:
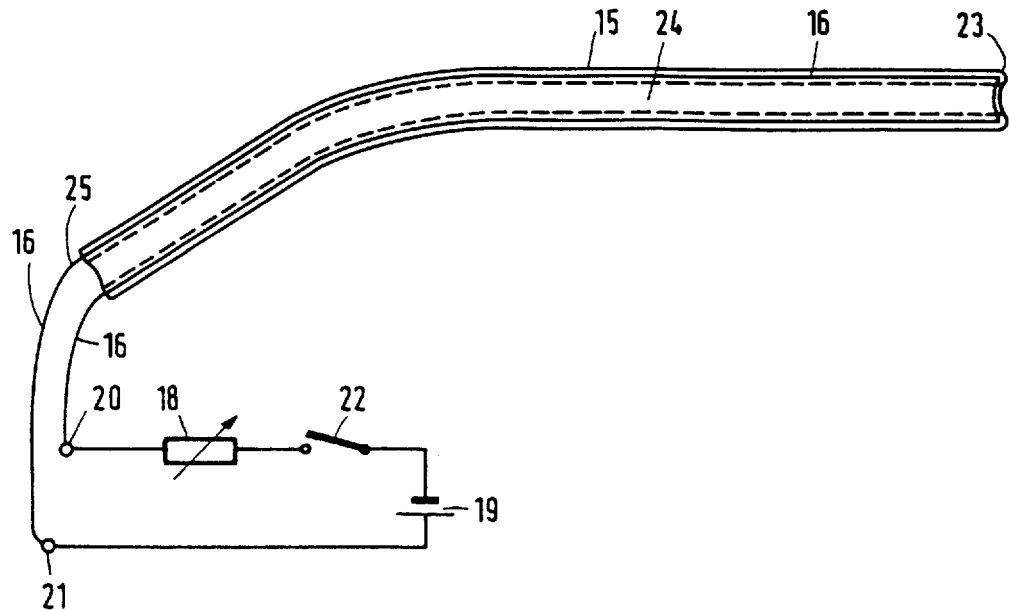
FIG. 2 shows a catheter comprising a conductor loop.

FIG. 2 shows the catheter 15 with the conductor loop 16 in accordance with the invention. The catheter 15 is made of an electrically suitably insulating material having a low magnetic susceptibility. The catheter 15 has a fixed diameter which is, for example between 0.3 mm and 3 mm and also has a fixed length which may be, for example 110 cm or 150 cm. For the remainder the catheter 15 has a customary shape and construction and comprises a distal end 23 to be introduced into, for example a blood vessel of the patient. The catheter 15 also comprises a customary duct 24 and proximal end 25 where through, for example, instruments can be introduced into the patient or where through, for example, thinner catheters or guide wires for controlling the catheter 15 can be inserted. Furthermore, contrast media or active substances, for example thrombolytic liquids, can also be administered via the catheter 15. The conductor loop 16 is provided directly underneath the surface and adjacent the duct 24 in the catheter 15. The conductor loop 16 consists of a nonmagnetic conductive materials for example copper wire, having a diameter of, for example 0.1 mm. The conductor loop 16 is provided underneath the surface along substantially the entire length of the catheter 15. The conductor loop 16 is connected to a voltage source 19 via a first variable resistor 18 and a first switch 22. The additional magnetic field is adjusted by adjustment of the current through the conductor loop 16 by means of the variable resistor 18. Furthermore, the strength of the additional magnetic field is determined by the distance between the first conductor 20 and the second conductor 21 of the conductor loop 16.

Figure 3:
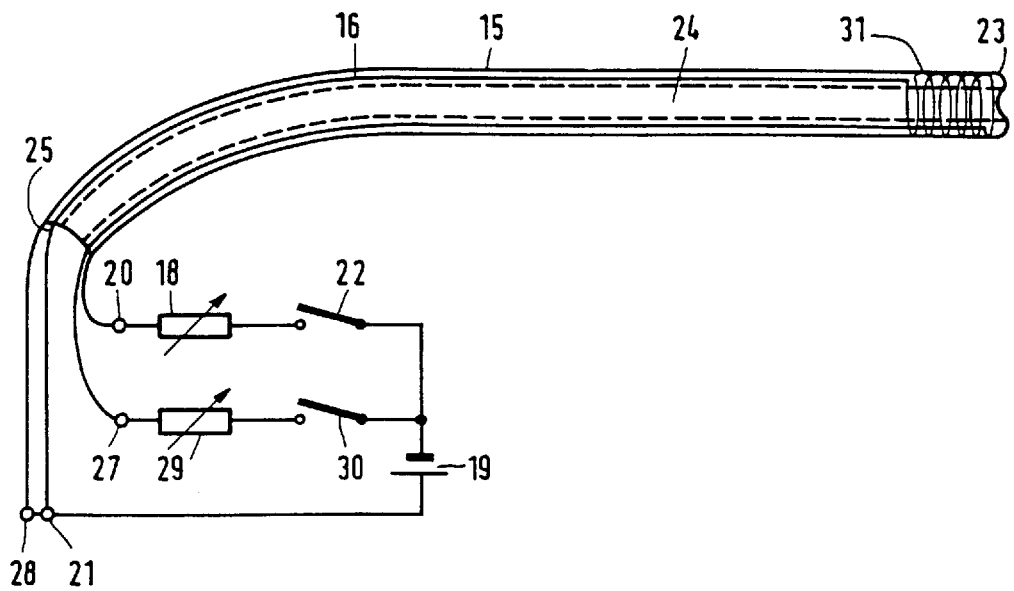
FIG. 3 shows a catheter comprising a conductor loop and a coil.

In a further embodiment of the invention, the catheter comprises a coil 31 in addition to the conductor loop 16. The contrast of an image of the coil can be adjusted separately from the contrast of the catheter when the current is applied to the coil via separate conductors. A catheter of this kind will be described in detail with reference to FIG. 3. FIG. 3 shows a coil 31 which is provided underneath the surface of the catheter 15, for example near the distal end 23. The coil 31 may be constructed as, for example a saddle-coil provided near the exterior of the catheter. The coil 31 is connected to the voltage source 19 via separate conductors 27, 28 and a second variable resistor 29 and a second switch 30. The second additional magnetic field is adjusted by adjustment of the current through the coil 31 by means of the second variable resistor 29. Another possibility consists in connecting the coil 31 in series or in parallel with the conductor loop 16, the number of turns and the diameter of the turns and the shape of the coil then determining the difference in contrast with respect to the remainder of the catheter; however, in that case separate control of the coil contrast is not possible relative to the contrast of the remainder of the catheter. Moreover, several other coils can be provided in different locations on the catheter, each of said other coils generating an additional magnetic field so that the various locations can be imaged in an MR image.

The position of the catheter 15 can be determined in various ways. A first way is, for example by determining the position of the catheter 15 with the conductor loop 16 from an MR image. A second way is by determining a position of a location of the catheter in which the coil 31 is provided, for example the distal end 23, from successive 1D projection signals.

According to the first way, a current is adjusted through the conductor loop 16 during the generating of MR signals for the reconstruction of an MR image. This produces a first additional magnetic field in the vicinity of the conductor loop. If the disturbance by the first additional magnetic field is sufficiently large, the disturbance and hence the catheter will be imaged in the MR image. The contrast with which the catheter is imaged with respect to the surrounding tissue can be adjusted, for example by increasing the value of the current through the conductor loop. If the disturbance is not visible, an image of the catheter 15 can be derived from two successive images by the image processing unit 12. To this end, during the generating of MR signals for determining a first image the additional magnetic field along the conductor loop 16 in the catheter is absent, whereas it is present during the generating of the MR signals for determining a next image. An image and a position of the catheter 15 are derived from the differences between the two MR images by the image processing unit 12. Subsequently, the image of the catheter can be reproduced in the first MR image on the monitor 14. During the generating of MR signals the additional magnetic field of the conductor loop 16 can be activated by means of a control signal from the control unit 13 which is connected to the catheter control unit 17 for this purpose. The positioning accuracy can be further improved when during the generating of the MR signals for a first image a disturbance is caused by the additional magnetic field under the influence of a current in a first direction and during the generating of the MR signals for a next image a disturbance is caused by the additional magnetic field under the influence of a current in a direction opposing said first direction. In order to track the displacement of the catheter during the intervention on the basis of MR images, the catheter position determined can be used to adjust the region of a next MR image to be imaged. To this end, the position is applied to the control unit 13.

The MR image acquisition time can be reduced by utilizing, for example a so-called keyhole method. A keyhole method is known from the patent application EP-A 25 543468. According to the keyhole method disclosed in the patent application an MR signal set associated with a complete k-space is used so as to obtain a first reference image. In order to obtain a next image, for only a part of the k-space new MR signals are generated. The MR signals received are subsequently substituted in the positions of the MR signals associated with this part of the k-space previously obtained and stored in a memory of the image reconstruction unit 11. The image reconstruction unit 11 subsequently determines the next image from the updated MR signal set.

In order to determine the position of the distal end 23 of the catheter 15 from successive 1D projection signals, the control unit 13 successively generates control signals for generating successive series of three 1D projection signals for the three orthogonal main axes, for example the x-axis, the y-axis and the z-axis, the current through the coil 31 being switched off during the generating of a first series of 1D projection signals whereas it is the current through the coil 31 is switched on during the generating of a second series of 1D projection signals. Proton density profiles are obtained from the 1D projection signals by way of successive 1D Fourier transformations.

Figure 4:
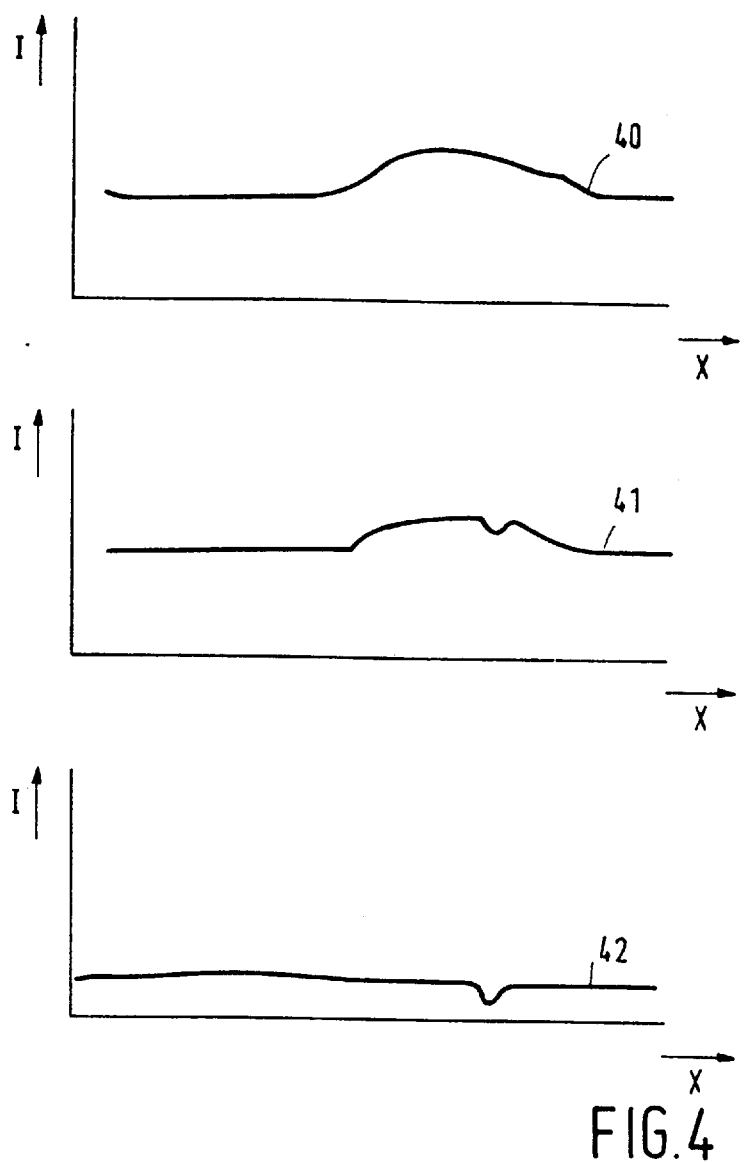
FIG. 4 illustrates a position determining operation utilizing one-dimensional proton density profiles.
Figure 5:
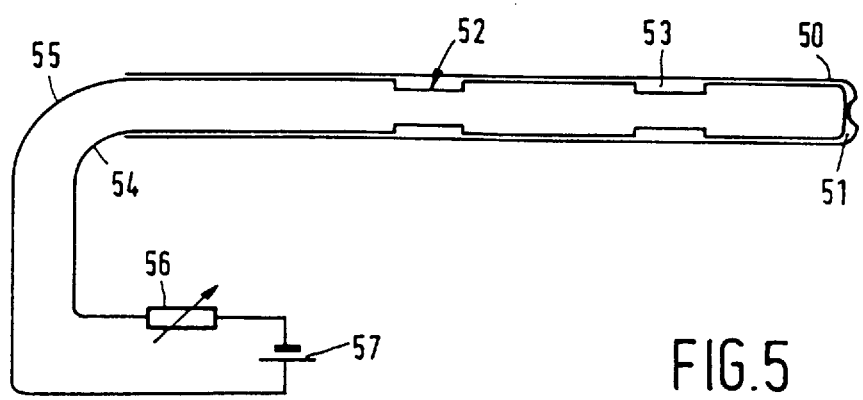
FIG. 5 shows a conductor loop formed by conductors having two different distance between each other.

FIG. 4 shows an example of two temporally successive proton density profiles 40 and 41 along the same main axis. The first proton density profile 40 does not include a disturbance whereas the second proton density profile 41 includes the disturbance. The position 42 of a deviation along, for example the first main axis is determined from the difference between the proton density profiles 40 and 41. The position of the deviation on the other two main axes is determined in a similar manner, the position of the distal end 23 of the catheter 15 in the body 7 thus being determined. The 1D Fourier transformations and the determination of the differences between the proton density profiles are executed by the image reconstruction unit 1. The position of the distal end 23 of the catheter 15 thus determined can be visualized on the monitor 14 by means of a cursor; moreover, it can also be used for continuously tracking the catheter 15 in an MR image. To this end, the position of the catheter 15 is applied to the control unit 13. The control unit 13 subsequently adapts the position of the region of the body to be imaged so that, for example the distal end 23 of the catheter 15 remains visible in the image. By varying the distance between the conductors in some parts of the catheter the magnetic field can be disturbed in a predetermined pattern. This pattern enables a better recognizability of the catheter in an MR-image. A catheter with different distances between some of the conducting parts is shown in FIG. 5. FIG. 5 shows the catheter 50 with a conductor loop 51 in accordance with the invention. Further the distance between a first conductor 54 and a second conductor 55 of a first part 52 and the distance between the first conductor 54 and a second conductor 55 of a second part 53 are equal, but different from the distance of the conductors outside the two parts 52, 53. Therefore the extra magnetic field nearby the first part 52 and the second part 53 will be different from the extra magnetic field nearby the remainder of the catheter 50. Consequently a pattern around the catheter will be visible in an MR-image. Further a variable resistor 56 and a power supply 57 are connected with the catheter 50. With the variable resistor 56 the current through the conductor loop 51 could be controlled and consequently the contrast of the catheter in the MR-image. To reduce HF disturbances both conductors could also be curled around the long axis of the catheter.

For example a catheter with a conductor loop 17 comprising conductors curled in a helix configuration. Catheters with these helix configuration conductor loops are explained with reference to FIG. 6, 7, 8 and 9.

Figure 6:
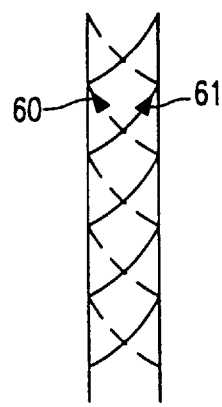
FIG. 6 shows a conductor loop curled in a parallel helix configuration.

FIG. 6 shows a catheter 16 with conductor loop 17 having a parallel helix configuration, in which both conductors 60, 61 of the conductor loop are parallel to each other.

Figure 7:
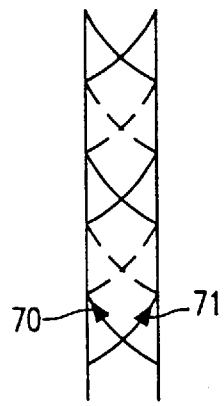
FIG. 7 shows a conductor loop curled in a anti-parallel helix configuration.

FIG. 7 shows a catheter 15 with the conductor loop 17 in an anti-parallel helix configuration in which the conductors 70, 71 cross each other. An advantage of the anti-parallel helix configuration is that the torsion on the catheter due to electromagnetic forces on the conductors 70, 71 is reduced with respect the torsion on a catheter due to the electromagnetic forces on the conductors 60, 61 in a parallel helix configuration. These electromagnetic forces are generated when a current is directed through the conductor loop in the static magnetic field.

Figure 8:
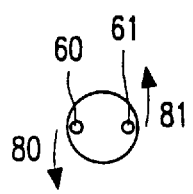
FIG. 8 shows the direction of electromagnetic forces on the conductors in a parallel helix configuration.

FIG. 8 shows the forces on the conductors 60, 61 of the conductor loop 16 in a parallel helix configuration. The arrows 80, 81 indicate the directions of the generated electromagnetic forces when a direct current is generated in the conductor loop. The directions of the forces are pointed in opposite directions and introduce a torsion on the catheter.

Figure 9:
FIG. 9 shows the direction of electromagnetic forces on the conductors in an anti-parallel helix configuration.

FIG. 9 shows the directions of the forces on the conductors 70, 71 of a conductor loop curled in the anti-parallel helix. The arrows 90, 91 indicate the directions of the forces when a direct current is directed through the conductor loop. Because the directions of the forces 37, 38 on the conductors 70, 71 are pointed in the same direction the torsion on the catheter 15 is substantially reduced.

We claim:

1. An MR system for interventional procedures, comprising an MR imaging device which is arranged to acquire images of a part of an object, said MR imaging device including a magnet for generating a steady magnetic field, and means for generating temporary magnetic gradient fields, and an elongated interventional instrument (i) which includes a conductor loop with two non-magnetic conductors being spaced apart along and extending along substantially the length of an operative portion of the instrument and (ii) which is arranged for application of a direct current through the conductor loop for generating a direct current through the conductor loop for generating a first additional magnetic field in the vicinity of and along substantially the length of the operative portion of the instrument, during acquisition of an MR image.

2. An MR system as claimed in claim 1, further comprising means for adjusting the amount of direct current through the conductor loop.

3. An MR system as claimed in claim 2, wherein the distance between the conductors along the instrument is different for some parts of the instrument.

4. An MR system as claimed in claim 2, wherein the conductors of the conductor loop are curled in a helix configuration.

5. An MR system as claimed in claim 2, wherein the conductors of the conductor loop are curled in a helix configuration.

6. An MR system as claimed in claim 1, wherein the interventional instrument is provided with a coil for generating a second additional magnetic field which deviates from the first additional magnetic field.

7. An MR system as claimed in claim 6, wherein the distance between the conductors along the instrument is different for some parts of the instrument.

8. An MR system as claimed in claim 1, wherein the distance between the conductors along the instrument is different for some parts of the instrument.

9. An MR system as claimed in claim 1, wherein the conductors of the conductor loop are curled in a helix configuration.

10. An MR system as claimed in claim 1, wherein the conductors of the conductor loop are curled in an anti-parallel helix configuration.

11. An MR system as claimed in claim 1, wherein the interventional instrument is provided with a coil for generating a second additional magnetic field which deviates from the first additional magnetic field.

12. An MR system as claimed in claim 11, wherein the distance between the conductors along the instrument is different for some parts of the instrument.

13. An MR system as claimed in claim 1, wherein the MR imaging device further comprises means for determining the position of the interventional instrument from MR images.

14. An MR system as claims in claim 13 wherein the MR imaging device further comprises means for adjusting the region of the next MR images to be acquired according to the determined position of the interventional instrument.

15. An interventional MR method comprising:

a) generating MR signals in order to determine temporally successive first and second MR images, b) generating at least one additional magnetic field in the vicinity of and along substantially the length of the operative portion of the instrument, during the generating of MR signals for determining the second MR image by applying a direct current through a conductor loop in an interventional instrument, the conductor loop comprising two non-magnetic conductors being spaced apart along and extending along substantially the length of c) receiving the MR signals generated, d) processing the MR signals received so as to form the first and second MR images, and e) determining a position of the instrument within the object on the basis of the first and second MR images.

16. An interventional MR method as claimed in claim 15, characterized in that the MR signals generated are in accordance with a so called keyhole technique in which a complete scan of k-space is done to obtain a first reference image and only a portion of k-space is scanned for a next image, which is used to update the reference image.

17. An instrument for penetrating a body in cooperation with examination of the body with an MR device, said instrument comprising a conductor loop with two non-magnetic conductors being spaced apart alone and extending along substantially the length of an operative portion of the instrument for generating a first magnetic field in the vicinity of and along substantially the length of the operative portion of the instrument, in response to direct current in said conductor loop.

18. An instrument as claimed in claim 17, further comprising means for adjusting the amount of direct current through the conductor loop.

19. An instrument as claimed in claim 17, wherein the conductors of the conductor loop are curled in a helix configuration.

20. An instrument as claimed in claim 17, wherein the conductors of the conductor loop are curled in an anti-parallel helix configuration.

21. An instrument as claimed in claim 17, further comprising a coil for generating a second additional magnetic field which deviates from the first additional magnetic field.

* * * * *